US009220653B2

(12) United States Patent
Israel

(10) Patent No.: US 9,220,653 B2
(45) Date of Patent: Dec. 29, 2015

(54) METHOD AND DEVICE FOR IMPROVING TEMPOROMANDIBULAR JOINT RANGE OF MOTION AND STRENGTHENING/MASSAGING JAW MUSCLES

(75) Inventor: Howard A. Israel, Great Neck, NY (US)

(73) Assignee: Therapeutic Mobilization Devices, L.L.C., Great Neck, NY (US)

( * ) Notice: Subject to any disclaimer, the term of this patent is extended or adjusted under 35 U.S.C. 154(b) by 346 days.

(21) Appl. No.: 14/006,689

(22) PCT Filed: Aug. 13, 2012

(86) PCT No.: PCT/US2012/050538
§ 371 (c)(1),
(2), (4) Date: Sep. 23, 2013

(87) PCT Pub. No.: WO2013/025587
PCT Pub. Date: Feb. 21, 2013

(65) Prior Publication Data

US 2014/0018710 A1 Jan. 16, 2014

Related U.S. Application Data

(60) Provisional application No. 61/523,446, filed on Aug. 15, 2011.

(51) Int. Cl.

| | |
|---|---|
| ***A61M 11/00*** | (2006.01) |
| ***A61H 1/02*** | (2006.01) |
| ***A61H 9/00*** | (2006.01) |

(52) U.S. Cl.
CPC ................ *A61H 1/02* (2013.01); *A61H 9/0078* (2013.01); *A61H 2201/0207* (2013.01);

(Continued)

(58) Field of Classification Search
CPC ............. A61F 5/566; A61F 5/56; A61F 5/00; A61F 2005/563; A61H 1/02; A61H 9/0078; A61H 2201/0207; A61H 2201/0214; A61H 2201/1238; A61H 2201/165; A61H 2201/1664; A61H 2201/1676; A61H 2205/026
USPC ......................................... 128/845, 848, 861
See application file for complete search history.

(56) References Cited

U.S. PATENT DOCUMENTS 3,813,096 A 5/1974 Welch
4,280,696 A 7/1981 Ramon (Continued)

OTHER PUBLICATIONS

"TheraBrite® Jaw Motion Rehabilitation System," Brochure of Atos Medical AB, Hörby, Sweden (undated).

(Continued)

*Primary Examiner* — Steven Douglas
(74) *Attorney, Agent, or Firm* — David M. Quinlan, P.C.

(57) ABSTRACT

A therapeutic exercising device that can simultaneously increase temporomandibular joint range of motion and strengthen jaw muscles comprises two bite members with bite portions for insertion between a user's teeth and a bellows between the bite members that moves them relative to each other toward an open position that separates the user's upper and lower jaws. A spring exerts a predetermined opening force on the bite members open, and one or more elastic members attached between the bite members exert an opposing closing force. A user-operated pneumatic pump introduces air under pressure into the bellows to open the bite members when the closing force is sufficient to overcome the opening force. The device can be used with air bladders that massage the jaw muscles, with the optional application of heat or cold. The device is usable with a mandible translation adapter to exercise a user's mandible in the posterior-anterior direction.

14 Claims, 9 Drawing Sheets

(52) U.S. Cl.

CPC .................. *A61H 2201/0214* (2013.01); *A61H 2201/1238* (2013.01); *A61H 2201/165* (2013.01); *A61H 2201/1664* (2013.01); *A61H 2201/1676* (2013.01); *A61H 2205/026* (2013.01)

(56) References Cited

U.S. PATENT DOCUMENTS

| | | | |
|---|---|---|---|
| 4,834,112 | A | 5/1989 | Machek et al. |
| 4,938,230 | A | 7/1990 | Machek et al. |
| 5,035,420 | A | 7/1991 | Beeuwkes, III et al. |
| 5,158,096 | A | 10/1992 | Clark et al. |
| 5,183,057 | A | 2/1993 | Syrop et al. |
| 5,365,945 | A | 11/1994 | Halstrom |
| 5,374,237 | A | 12/1994 | McCarty, Jr. |
| 5,427,117 | A | 6/1995 | Thornton |
| 5,562,105 | A | 10/1996 | Syrop et al. |
| 5,582,560 | A | 12/1996 | Magnuson |
| 5,846,212 | A | 12/1998 | Beeuwkes, III et al. |
| 6,050,961 | A | 4/2000 | Arnold |
| 6,126,683 | A | 10/2000 | Momtaheni |
| 6,155,262 | A | 12/2000 | Thornton et al. |
| 6,361,475 | B1 | 3/2002 | Jobe |
| 6,413,231 | B1 | 7/2002 | Berman et al. |
| 6,558,392 | B1 | 5/2003 | Martini |
| 6,562,060 | B1 | 5/2003 | Momtaheni |
| 6,604,527 | B1 | 8/2003 | Palmisano |
| 7,238,145 | B2 | 7/2007 | Robbins et al. |
| 7,520,281 | B1 | 4/2009 | Nahabedian |
| 2007/0012319 | A1 | 1/2007 | Frascati et al. |
| 2007/0037665 | A1 | 2/2007 | Robbins et al. |
| 2007/0089752 | A1 | 4/2007 | Christensen, III |
| 2007/0287598 | A1 | 12/2007 | Christensen, III |
| 2010/0011916 | A1 | 1/2010 | Christensen, III |
| 2010/0316973 | A1 | 12/2010 | Remmers et al. |
| 2010/0322454 | A1 | 12/2010 | Ambrose et al. |

OTHER PUBLICATIONS

“E-Z Flex™ Jaw Exerciser,” Brochure of Fluid Motion Biotechnologies, Inc., New York, NY (1996).

Tiwari, Bhawana et al., “A New Dynamic Jaw Exerciser,” Indian Jour. of Dental Sciences, vol. 2, No. 2, pp. 4-6 Mar. 2010.

www.craniorehab.com, “Orastretch Press Jaw Motion Rehab System” and “Jaw Motion Rehab System Comparison,” last visited Jan. 29, 2010.

Lin, Tsung-yin et al., “Patents Analysis and Design Suggestions for the Mandibular Advancement Devices,” Int’l Jour. of Biological Sci., vol. 6, pp. 103-108 (2012).

Written Opinion, PCT/US12/50538, Jan. 11, 2013.

METHOD AND DEVICE FOR IMPROVING TEMPOROMANDIBULAR JOINT RANGE OF MOTION AND STRENGTHENING/MASSAGING JAW MUSCLES

CROSS-REFERENCE TO RELATED APPLICATION

This application claims the benefit of U.S. provisional application No. 61/523,146, filed Aug. 15, 2011, which application is incorporated herein by reference.

BACKGROUND OF THE INVENTION

1. Field of the Invention

The present invention relates generally to providing therapy to the region of the jaw, and more particularly, to devices and methods for increasing temporomandibular joint range of motion while strengthening a user's jaw muscles, and for massaging the jaw muscles, optionally at the same time, and additionally to devices and methods for inducing forward mandibular translation for related therapeutic purposes.

2. Description of Related Art

Prior U.S. Pat. No. 5,183,057 and No. 5,562,105, on which I am named as a co-inventor, disclose a particularly effective device for improving temporomandibular joint range of motion. As noted in these related patents, this type of device is useful in many circumstances, one of the most important being as part of post-treatment therapy after medical procedures such as temporomandibular joint surgery, temporary intermaxillary fixation, facial infections, and trauma to the face, and as therapy for other medical conditions affecting the temporomandibular joint. One embodiment of the device uses a hollow bellows pump to force water into a bellows actuator between two hinged members placed between the user's teeth, thus separating the members and opening the user's mouth. The pump bellows is disposed in a separate housing, where it is compressed by a spring to force water into the actuator bellows. The user then bites down on the members to urge them together and force the water back into the pump bellows, after which the biasing spring operates to reopen the user's jaw. Repeatedly closing his or her mouth against the resistance provided by the spring exercises the temporomandibular joint and strengthens the user's jaw muscles.

This device is particularly effective and convenient when used solely in a mode in which the pump is operated by the user to passively stretch his or her jaw muscles to increase temporomandibular joint range of motion. In an embodiment of the patented device designed for that purpose, the hinged members are biased into a closed position and the user inserts the device into the mouth between the upper and lower jaws, after which the user manually squeezes the pump bellows to force the upper and lower jaws apart. When the pump bellows is released, the members are automatically returned to their closed position. But the embodiment described further above, which is designed also to strengthen the user's jaw muscles, is somewhat cumbersome to use and does not permit precise control of the resistance against which the user contracts the jaw muscles or the rate at which the user's jaw is reopened. These can be serious drawbacks since particular care must be taken when exerting these muscles in the circumstances in which the device is used, such as after temporomandibular joint surgery when the jaw is particularly vulnerable to damage if exercised too vigorously.

Other known devices used to manipulate a user's temporomandibular joint to increase range of motion, strengthen jaw muscles, or for other purposes, are shown in the following references:

| |
|---|
| U.S. Pat. No. 3,813,096 |
| U.S. Pat. No. 4,280,696 |
| U.S. Pat. No. 5,035,420 |
| U.S. Pat. No. 5,582,560 |
| U.S. Pat. No. 5,846,212 |
| U.S. Pat. No. 6,050,961 |
| U.S. Pat. No. 6,361,475 |
| U.S. Pat. No. 6,413,231 |
| U.S. Pat. No. 6,558,392 |
| U.S. Pat. No. 7,238,145 |
| U.S. Publ. No. 2007/0012319 |
| U.S. Publ. No. 2007/0089752 |
| U.S. Publ. No. 2007/0287598 |
| U.S. Publ. No. 2010/0011916 |

"TheraBite® Jaw Motion Rehabilitation System," Brochure of Atos Medical AB, Hörby, Sweden (undated).

"E-Z Flex™ Exerciser," Brochure of Fluid Motion Biotechnologies, Inc., New York, N.Y. (1996).

Tiwari, Bhawana, et al., "A New Dynamic Jaw Exerciser," *Indian Jour. of Dental Sciences*, Vol. 2, No. 2, pages 4-6 (2010).

None of these references discloses a device designed to increase temporomandibular joint range of motion in a manner precisely controlled by the user and at the same time strengthen jaw muscles by permitting repeated motion of the muscles against a calibrated resistance that the user can precisely adjust as part of a controlled exercise program.

Massage therapy can also be an effective treatment for temporomandibular joint and jaw muscle disorders, either alone or in combination with range of motion and/or strengthening exercises. While an individual can self-administer massage, most laymen are not trained in proper massage therapy techniques. Accordingly, self-massage in practice can be largely ineffective. By the same token, using a trained massage therapist can be expensive and inconvenient, and therefore not done with sufficient frequency to have maximum efficacy. Most individuals would likely find it preferable to be able to administer massage therapy themselves in a manner that they can be certain is safe and effective. It would be even more advantageous if massage therapy, with or without the application of heat or cold, could be administered in conjunction with exercises for improving temporomandibular joint range of motion and/or strengthening jaw muscles.

In addition to devices that involve opening and closing the mouth to exercise or administer therapy to jaw muscles, there are also devices that induce translation of the lower jaw ("mandible") back and forth (that is, in an anterior-posterior plane) to administer therapy to the jaw muscles and increase temporomandibular range of motion. The E-Z Flex™ jaw exerciser referred to above included a translation adapter that could be used to move the mandible forward for therapeutic reasons. U.S. Pat. No. 5,846,212 also discloses a mandible translator intended for therapeutic applications.

The mandibular translation device disclosed in U.S. Pat. No. 5,846,212 comprises two plates mounted for face-to-face sliding motion, with mouthpieces for the upper and lower teeth on the respective plates. That device and the translation adapter for the E-Z Flex™ jaw exerciser are operable only in a modality that requires user manipulation to return his or her mandible rearward to its natural position after being translated forward. In the case of the '212 patent, the user must directly manipulate the plates by hand to translate his or her mandible forward and backward. This gives rise to variations in the amount and/or rate of movement, which can be detrimental in some therapy regimens. In the E-Z Flex™ device the user has to exert a force with his mandible to translate it posteriorly. That may not be acceptable in some therapy regimens in which strictly passive mandible movement is indicated. Alternatively, the user can move the adapter with his or her hands to return the mandible to a non-protruding position, but that will be awkward with the adapter in the user's mouth and could cause injury to tissues associated with the temporomandibular joint.

A related issue involving mandibular translation is the treatment of obstructive sleep disorders, such as sleep apnea and snoring. A known treatment involves a user wearing a mandibular repositioning device that holds the mandible in a forward protruded position to prevent blockage of the airway to the lungs when the user is sleeping in a supine position. One of the issues in administering this type of therapy is properly fitting such devices to a particular user. Optimally, such devices hold the user's mandible in a forward position the minimum amount necessary to maintain the airway to the lungs open, without placing undue stress on the temporomandibular joint. It is known to pre-measure mandible translation during sleep tests prior to fitting such a device (see, for example, U.S. Pat. No. 6,155,262 and U.S. Publ. No. 2010/0316973), and to take diagnostic images of a user's jaw at different open positions (see for example, U.S. Pat. No. 4,834,112). But it is not known to pre-measure for the minimum amount of mandibular translation that should be imparted by a repositioning device while actually viewing the user's mouth parts as the mandible is held in a forward translated position.

SUMMARY OF THE INVENTION

It is an object of the present invention to improve on known devices and methods for increasing temporomandibular joint range of motion and increasing jaw muscle strength, simultaneously if preferred by a user, and also providing a temporomandibular joint/jaw muscle massage device that can be used either on its own or in conjunction with a temporomandibular joint/jaw muscle exercising device.

Thus, a first aspect of the invention relates to a therapeutic exercising device that can simultaneously increase temporomandibular joint range of motion and strengthen jaw muscles of a user. The device comprises a mouthpiece including two bite members, each having a bite platform for insertion into the user's mouth. An expandable enclosure, such as a bellows, expands and contracts between the bite members when air is introduced into and released from the interior of the enclosure. Expanding the enclosure exerts an opening force moving the bite members toward an open position in which they separate the user's upper and lower jaws. A predetermined force biases the bite members toward the open position. This spring biasing force is opposed by a user-adjustable biasing arrangement, which in one embodiment comprises a plurality of elastic members the user selectively attaches to the bite members. The user can attach a desired number of the elastic members to the bite members to exert on the bite members a closing force that will vary depending on the number of elastic members used. A user-operated pneumatic pump, such as a syringe, regulates the introduction of air into the expandable enclosure.

The user can operate this device in a number of ways. For example, the user can employ it as a combination temporomandibular joint range of motion exerciser and jaw muscle strengthening device by using an insufficient number of elastic members to hold the bite members normally closed. In this configuration, the user can manually close the bite members and insert them between his or her teeth. The bite members will be biased open, but the user can control the rate at which they open using the pump (syringe). Then, the user closes his or her mouth against the force biasing the members open to strengthen his or her jaw muscles. The force required to close the members is determined by the number of elastic members in place; that is, by reducing the number of elastic members the user can increase the force required to close the bite members. By attaching enough elastic members to bias the bite members closed, the device is used to increase temporomandibular joint range of motion by expanding the enclosure using the pump. The biasing members force the bite members to close at a rate that depends on the number of elastic members in place, as further controlled by the user via the pneumatic pump.

Another aspect of the invention relates to a therapeutic device for massaging a user's jaw muscles. This device comprises at least two hollow bladders that expand when air under pressure is introduced into their interiors and contract when the air under pressure is released. A wrap holds the bladders in place proximate to jaw muscles of the user, and a user-operated pneumatic pump, such as a syringe, introduces air under pressure into the bladders to expand the bladders and thereby compress jaw muscles of the user. The user reverses the motion of the pump to draw air from the bladders, and then repeats the process to administer a massaging action to the jaw muscles. In one preferred form, the device includes temperature adjusting pads held in place by the wrap against the user's face for applying heat or cold to jaw muscles as they are massaged.

In still another aspect of the invention, the exercising device and massaging device are used together. The pump can be designed to introduce air separately to the expandable enclosure (bellows), on the one hand, and to the bladders, on the other, to permit the user to optimize the combined exercising and massaging actions.

It is another object of the invention to provide a mandible translation adapter that can be used with the above described therapeutic exercising device to provide controlled mandibular forward (anterior) and backward (posterior) translation that is adaptable to a variety of exercise and therapy regimens. To that that end, a mandibular translation device comprises a mandible frame including a mandible actuating plate and a mandible actuating arm having a mandible retainer for engaging the user's mandible and a maxilla frame including a maxilla bearing plate and a maxilla contacting arm for engaging the user's maxilla. The frames move relative to each other in a first direction to protrude mandible anteriorly relative to the user's maxilla, and an adjustable biasing arrangement exerts a force determined by the user on the frames in a second direction opposite to the first direction. In one particular aspect of the invention, the exercising device with features as discussed above can be used to move the frames in the first direction.

In yet another aspect of the invention the mandible translation adapter is calibrated to indicate the amount of forward mandible translation and made of non-ferrous materials so that images can be taken of a user's mouth parts while the adapter is in place to determine the minimum amount of forward translation necessary to impart for the treatment of obstructive sleep apnea, snoring, and other conditions involving airway restriction, such as mandibular retrognathia (a retruded mandible), that are typically treated by performing surgical advancement of the mandible. This application of the device permits prediction of the placement of the retruded mandible prior to surgery into an ideal forward translated position.

This Summary is provided to introduce in a simplified form a selection of concepts relating to the subject matter described herein that are further described below in the Detailed Description of Preferred Embodiments. It is not intended necessarily to identify key or essential features of the invention, nor as an aid in determining the scope of the claimed subject matter.

BRIEF DESCRIPTION OF THE DRAWINGS

The objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

One skilled in the art will readily understand that the drawings are not strictly to scale, but nevertheless will find them sufficient, when taken with the detailed descriptions of preferred embodiments that follow, to make and use the present invention.

DETAILED DESCRIPTION OF PREFERRED EMBODIMENTS

As already noted, the invention has numerous aspects. One is a jaw exerciser that can be used as an active exercise device that strengthens jaw muscles by providing resistance against which the user closes his or her mouth, a passive exercise device that gently opens a user's mouth to restore or increase range of motion of the user's jaw, or a device that can function in both capacities at the same time. Another aspect is a jaw massager operated by the user to apply a gentle massaging action to jaw muscles for therapeutic effect, either with or without the application of heat or cold during the massage. In a third aspect, the jaw massager can be used in conjunction with the jaw exerciser to further enhance the beneficial effects of the invention for a user. In a fourth aspect, a mandible translation adapter for the jaw exerciser can be used in exercises and therapeutic applications in which the mandible moves forward from a normal position and back again. An optional use of the translation adapter permits optimal fitting of a mandibular repositioning device used in treating sleep disorders such as obstructive sleep apnea and snoring.

The detailed description that follows is intended to provide specific examples of particular embodiments illustrating various ways of implementing the claimed subject matter. It is written to take into account the level of knowledge of one of ordinary skill in the art to which the claimed subject matter pertains. Accordingly, certain details may be omitted as being unnecessary for enabling such a person to realize the embodiments described herein. It will also be understood that terms indicating direction or orientation, such as "lower," "upper," "top," "bottom," "left," right," etc., may be used to facilitate the description of these exemplary embodiments. The use of such terms does not imply that the claimed subject matter is limited to a particular orientation of the structure being described

Active/Passive Jaw Exerciser

Figure 1:
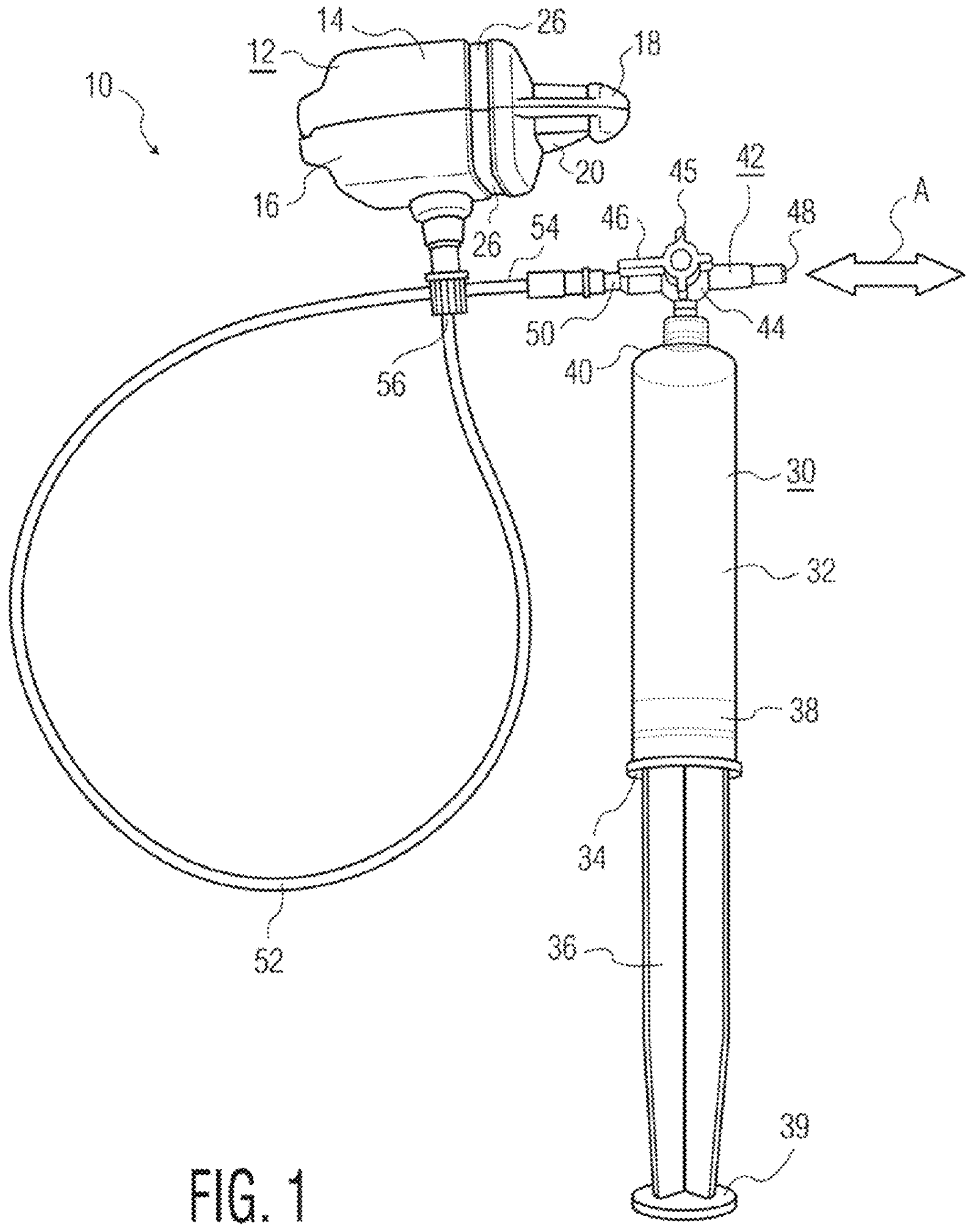
FIG. 1 is an isometric view of a therapeutic device for exercising a user's jaw muscles and/or increasing jaw range of motion, in accordance with one embodiment of the present invention.
Figure 2:
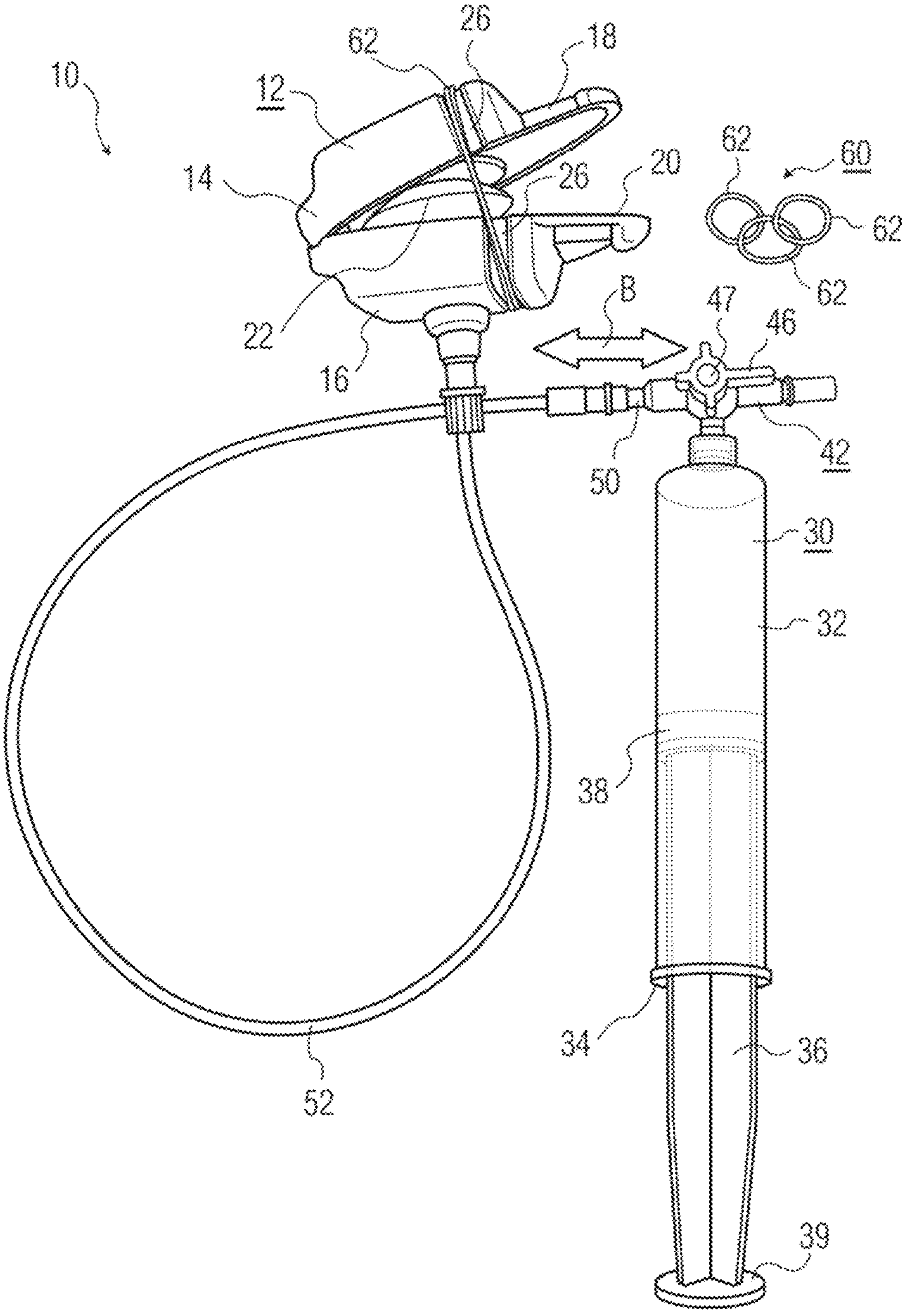
FIG. 2 is an isometric view of the therapeutic device shown in FIG. 1, further illustrating the different components rendering it capable of exercising jaw muscles and increasing jaw range of motion.
Figure 3:
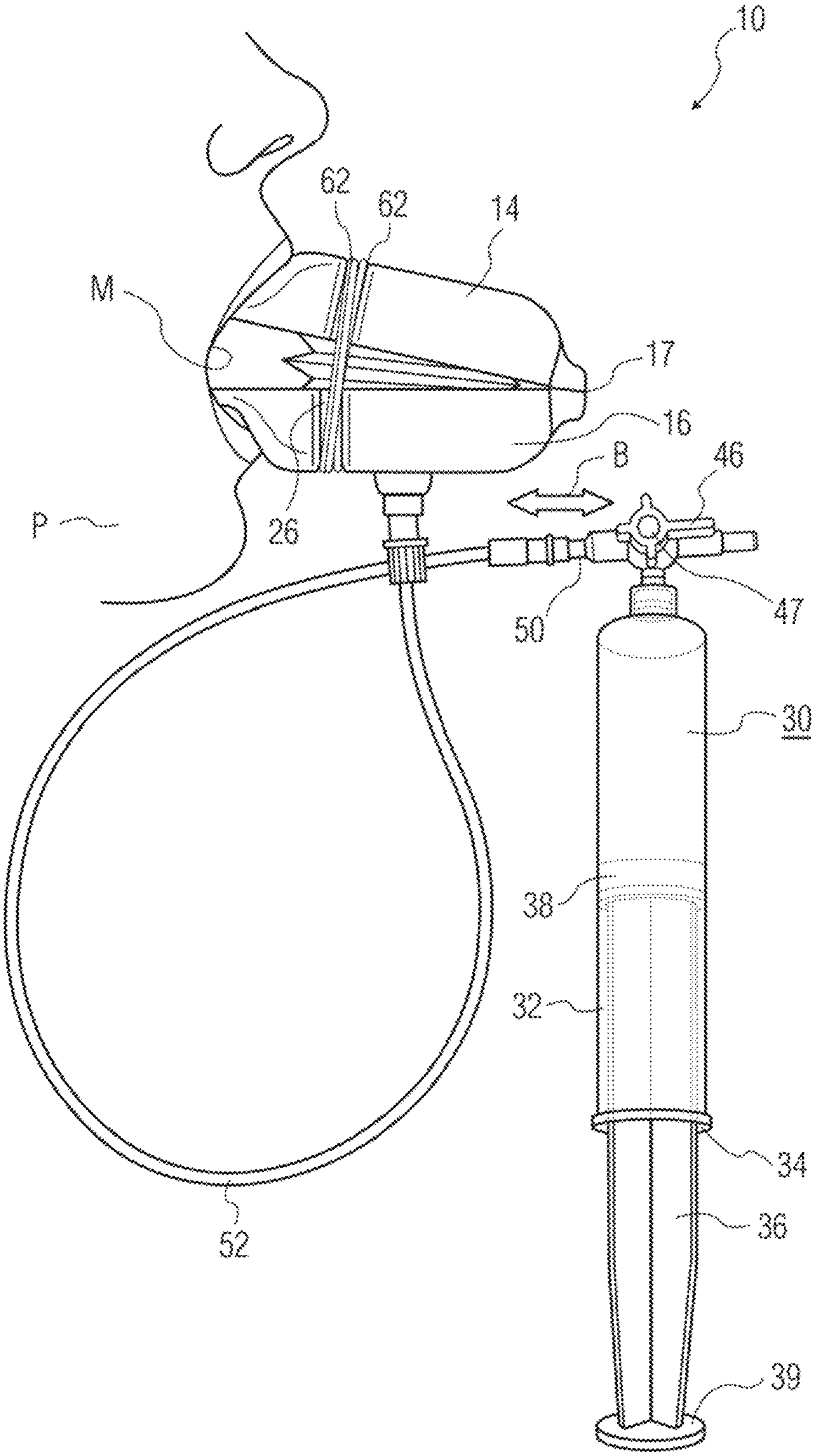
FIG. 3 is an isometric view of the therapeutic device in FIGS. 1 and 2 illustrating its use in exercising a user's jaw muscles and/or increasing jaw range of motion.

Referring first to FIGS. 1-3, an embodiment according to a first aspect of the invention comprises a therapeutic jaw exercising device 10. The device includes a mouthpiece 12 that includes a first bite member 14 and a second bite member 16 that are connected together at a hinge 17 (FIG. 3) for rotation between a closed position (FIG. 1) and an open position (FIG. 2). The first bite member 14 has an first bite platform 18 and the second bite member 16 has a second bite platform 20 that fit between the user's maxillary and mandibular dentition, as shown in FIG. 3. The first bite member and bite platform are sometimes referred to herein with the label "upper" and the second bite member and bite platform are likewise sometimes referred to herein with the label "lower." It is understood that this is meant only to reflect the manner in which the device is used as described herein and depicted in the drawings. It will be understood as the description proceeds that these labels are not limiting and that the device can be used with the first bite platform in contact with the user's lower (mandibular) dentition and the second bite platform in contact with user's upper (maxillary) dentition.

Referring particularly to FIG. 2, which shows the bite members in their open positions, an expandable bellows 22 is visible inside the mouthpiece 12. The natural resilience of the material from which the bellows 22 is made acts as a spring to bias the bite members 14 and 16 into their open positions shown in FIG. 2. Optionally, a separate spring can be provided at any convenient location to provide an additional bias-open force on the bite members, and those skilled in the art will immediately recognize that any suitable arrangement can be used to bias the bite members toward their open positions. In a preferred construction the bias-open force will be applied directly to the bite members 14 and 16, for example, by one or more compression springs (not shown) located between the upper and lower bite members 14 and 16. The bias-open force can be provided in any suitable fashion, such as one or more torsion springs (not shown) placed inside the mouthpiece at the hinge 17, or elastic members (not shown) The upper and lower bite members 14 and 16 have grooves 26 for a purpose described further below.

Figure 1A:
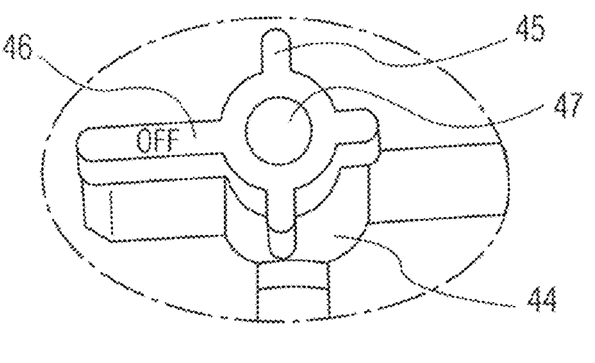
FIG. 1A is an enlarged view of a valving arrangement used in operating the device.

The device 10 further includes a pneumatic pump, taking the form of a syringe 30 in the present embodiment. The hollow cylindrical body platform 32 of the syringe has an open end 34 that accepts a plunger 36 that slides inside the body 32, in sealing relation thereto through the seal 38 at the end of the plunger disposed within the body 32. At its other end outside the plunger body 32 the plunger includes a handle 39 by which a user can operate the plunger 36 by sliding it to and fro within the cylindrical platform. (Typically, the plunger 36 will be removable from the syringe body 32 for replacement or cleaning.) The otherwise closed end 40 of the syringe body 32 is connected in airtight fashion to a valving arrangement 42, shown in more detail in FIG. 1A. The valving arrangement includes a valve body 44 and a valve actuator 45 having a manually operable valve handle 46 rotatable relative to the valve body about an axis 47. The valve handle 46 has the word "OFF" engraved or otherwise printed on it to assist in operating the device in the manner discussed in detail further below. The valve body includes an ambient air passage 48 and a bellows air passage 50. A tube 52 has one end 54 connected in airtight relation to the valve passage 50. The other end 56 of the tube is connected to the mouthpiece in airtight relation with the interior of the expandable bellows 22.

Finally, the device includes a user-adjustable biasing arrangement 60 that in the present embodiment comprises a plurality of elastic members 62 that resemble rubber bands, although they may be made of different materials for reasons related to their use in the present invention. For example, it may be necessary to make the elastic members of a material that accounts for any allergies of a user. It is also preferable to make the elastic members of dimensions and of a material that will provide a precise amount of force when in place on the mouthpiece. In addition, the material should be chosen so that the amount of force each elastic band exerts when it place will remain substantially constant over a period of time during which the device is used. An example of a suitable material is silicone, latex-free elastic. In use the elastic members fit into the grooves 26 on the upper and lower bite members 14 and 16. They are under tension when in place and each provides a predetermined amount of force biasing the bite members toward their closed position, against the force of the spring discussed above that provides a biasing force tending to separate the bite members. The therapeutic jaw exercising device 10 can be set up in two basic configurations. In one the closing force on the bite members 14 and 16 exerted by the adjustable biasing arrangement 60 (comprising one or more elastic bands in the present embodiment) is insufficient to hold the bite members closed against the built-in force biasing them open. The device in this configuration will be referred to for convenience as the "active jaw exerciser." In the other basic configuration the adjustable biasing arrangement 60 hold the bite members closed against the built-in force biasing them open. The device in this configuration will be referred to for convenience as the "passive jaw exerciser." It will be understood that this terminology is for ease of reference only, and is not limiting as the manner is which the device can be used in any particular configuration.

Active Jaw Exerciser

As just noted, in this configuration the closing force provided by the elastic members 62 in place in the grooves 26 is insufficient to hold the bite members closed against the built-in force biasing them toward their open positions. In this configuration one or more of the elastic members 62 are placed in the grooves 26 as shown in FIGS. 2 and 3. The bite members 14 and 16 will preferably then be moved to their closed positions before the user places the bite platforms between his or her teeth.

To appreciate one way this can be done, consider the valving arrangement 42 connecting the interior of the syringe body 32 to the interior of the expandable bellows 22 through the tube 52. As already noted, the valve handle 46 is rotatable about its axis 47 to a first position shown in FIG. 1. In this position the valve prevents communication between the interior of the syringe body 32 and the tube 52, as indicated by the "OFF" indicated on the valve handle 46, and permits air flow between the syringe body 32 and the ambient air passage 48, as indicated by the arrow A. The valve handle 46 is also rotatable to a second position shown in FIGS. 2 and 3 in which the interior of the syringe body communicates through the bellows air passage 50 and the tube 52 to the interior of the bellows 22, as indicated by the arrow B. In this position, the interior of the syringe body and the interior of the bellows are sealed against the introduction of ambient air, which is visually indicated by the OFF indicia on the valve handle 46. If the valve handle 46 is placed in an intermediate position (not shown in the drawings) pointing downward toward the syringe, the valve passages 48 and 50 are in fluid communication, thus connecting the interior of the bellows to ambient air.

Thus, if the user places the valve handle 46 in this intermediate position (with the valve handle 46 pointing downward), the bite members can be squeezed together by hand against the force biasing them apart, without causing the syringe plunger to move. The syringe plunger 36 is placed at a location intermediate its travel in the syringe body 32 while the valve handle 46 is in the first position (FIG. 1), which communicates the interior of the syringe body 32 with ambient air. The user then rotates the valve handle 46 into the second position (FIGS. 2 and 3) to place the syringe body in airtight communication with the expandable bellows 22. As seen particularly in FIG. 3, this would permit the user P also to hold the bite members 14 and 16 closed with the syringe plunger in addition to gripping it with his or her hands while inserting the bite platforms 18 and 20 into his or her mouth M between the teeth. Once the bite platforms are in place between the teeth, the user controls the plunger travel into the syringe body to control the rate at which the bite members passively open the jaw. A suitably configured stop (not shown) can be included to limit the plunger stroke to prevent the user from depressing the plunger too far and injuring the user's jaw. This is the passive stroke of the device in this configuration.

An alternate manner of setting up the device to use it in the active jaw exerciser mode is by initially moving the valve handle 46 to its first position (see FIG. 1) to place the syringe body into fluid communication with ambient air. The plunger 36 is then moved by the user to an approximate intermediate position of its total stroke, but preferably closer to the syringe body closed end than its open end. Then, the valve handle 46 is moved to place the syringe body interior in fluid communication with the bellows 22 (see, for example, FIGS. 2 and 3). Since the syringe body is now in fluid-tight communication with the expandable bellows 22, moving the syringe plunger 36 will move the bite members 14 and 16, and vice versa. In the present configuration of the device, the bite members are biased open, and the user can close them by moving the syringe plunger 36 in a direction outwardly of the syringe body without requiring the user to manually squeeze the bite members together. This would make the device accessible in the active jaw exerciser mode to users that might not be able to provide sufficient force to the bite members to close them enough to get the bite platforms between their teeth, since the bite members can then be placed in the user's mouth while they are held closed using the syringe plunger. After the bite platforms are in place, the user uses the plunger to control the rate at which they open and force the jaws apart. Once the bite members have been thus opened, active strengthening jaw muscle exercises can be performed by applying a bite force on the upper and lower bite members using the jaw muscles.

Additionally, the user may wish to increase jaw range of motion in connection with recovering from a medical procedure after which the jaw muscles are inflamed or otherwise limited in the amount of stress to which they can be subjected. Accordingly, the device in this mode provides substantial flexibility of application by enabling a user to generate controlled passive jaw motion to increase range of motion in the early stages of a rehabilitation program, and then to strengthen the jaw muscles and improve jaw function as the rehabilitation progresses.

In that regard, it will be appreciated that a particular advantage of the device resides in the ability of the user to set the amount of force needed to close the bite members against the force biasing them open. This is done by using a different number of elastic members 60. If more members are used, then less force need be applied by the jaw muscles to close them. If the device is provided with elastic bands having predetermined properties, then a health care professional can instruct the patient to use a particular number of members adapted to the patient's condition. In an alternate embodiment, different members could have different properties and be color coded to indicate the degree of biasing force each one provides. In that case the patient would be instructed to use an elastic member of a particular color in his or her therapy. An alternate manner of increasing the force required to close the bite members would be by manually resisting closure using the syringe.

In the above configuration, the device both strengthens jaw muscles by having the user close his or her mouth against a resistance provided as discussed above, and passively exercises the jaw joint and jaw muscles of the user and increases their range of motion as the bite members are permitted to open. In addition, the device permits the user to adjust the force needed to close the bite members, as well as control the rate at which they are permitted to open.

Passive Jaw Exerciser

To set up the device in this configuration, a sufficient number of elastic bands 60 are used to overcome the built-in force biasing the bite members into their open positions. Alternatively, a single, optionally color-coded elastic band made specifically for that purpose could be included to make the device more convenient to use. In any case, the user rotates the valve handle 46 to its first position (FIG. 1) to place the interior of the syringe body 32 into communication with ambient air and draws the syringe plunger 36 to a position somewhat proximate to the outward end of its stroke. The valve handle is then rotated to the second position (FIG. 2), which places the syringe body interior into airtight communication with the interior of the bellows 22 through the tube 52. With the bite platforms between the user's teeth, the user can push the plunger 36 in to open the bite members as far as is desired and then use the plunger to permit them to close at a rate the user is comfortable with or just permit the elastic member or members to close them passively.

Of course, the above only describes one embodiment of an active/passive jaw exercise device according to the present invention. It will be appreciated by those skilled in the art that the purposes and effects of the invention can be realized by embodiments other than the one described above.

Numerous adaptations of the present embodiment are possible, providing the user with multiple options for jaw rehabilitation. Examples of adaptations and modifications other than any already alluded to include (but are not limited to) the following:

1. The bite members can be placed in an open position and further resistance to closure can be controlled by the user by holding pressure on the plunger while the user provides a biting force on the first and second bite members of the device;
2. A sustained passive opening stretch can be achieved for various lengths of time, by depressing the plunger to passively stretch the jaw open, then turning the valve to block air flow from the bellows to the body of the syringe; and
3. Progressively more passive stretching of the jaw can be achieved by obtaining the position described in "2" above (in which the barrel of the syringe is in fluid communication with ambient air), and then withdrawing the plunger by an amount that will draw more air into the syringe. During this operation, the valve maintains the sustained passive stretch described in "2." The valve handle can then be turned to the first position (FIG. 1) to place the syringe in fluid communication with the bellows, so that depressing the plunger will force more air into the bellows, thus increasing the separation of the first and second bite members and further increasing the opening of the jaw.

Jaw Muscle Massager (With Application of Hot or Cold Compresses)

Figure 4:
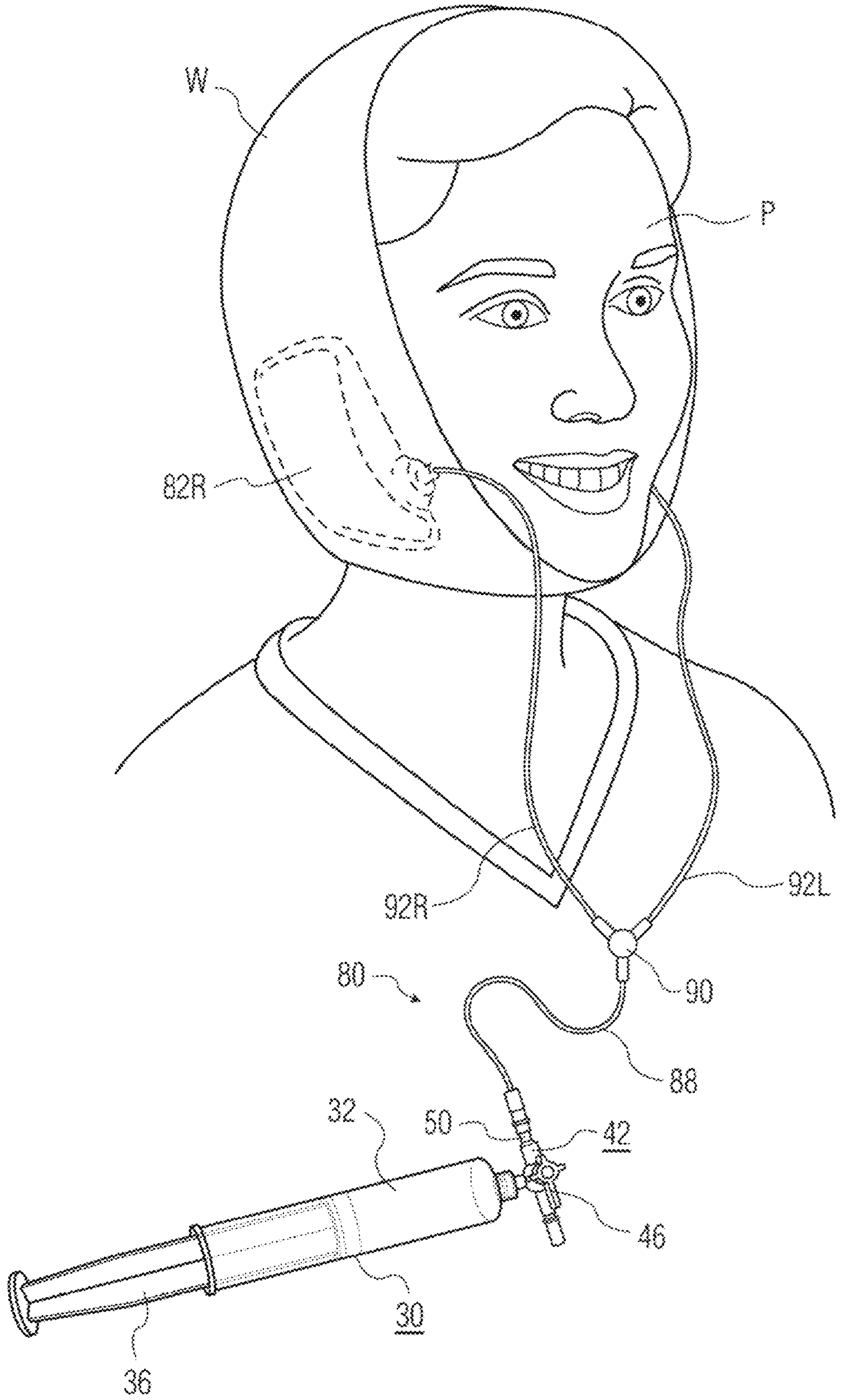
FIG. 4 is an isometric view illustrating the use of a therapeutic device for massaging jaw muscles in accordance with another aspect of the invention.
Figure 5:
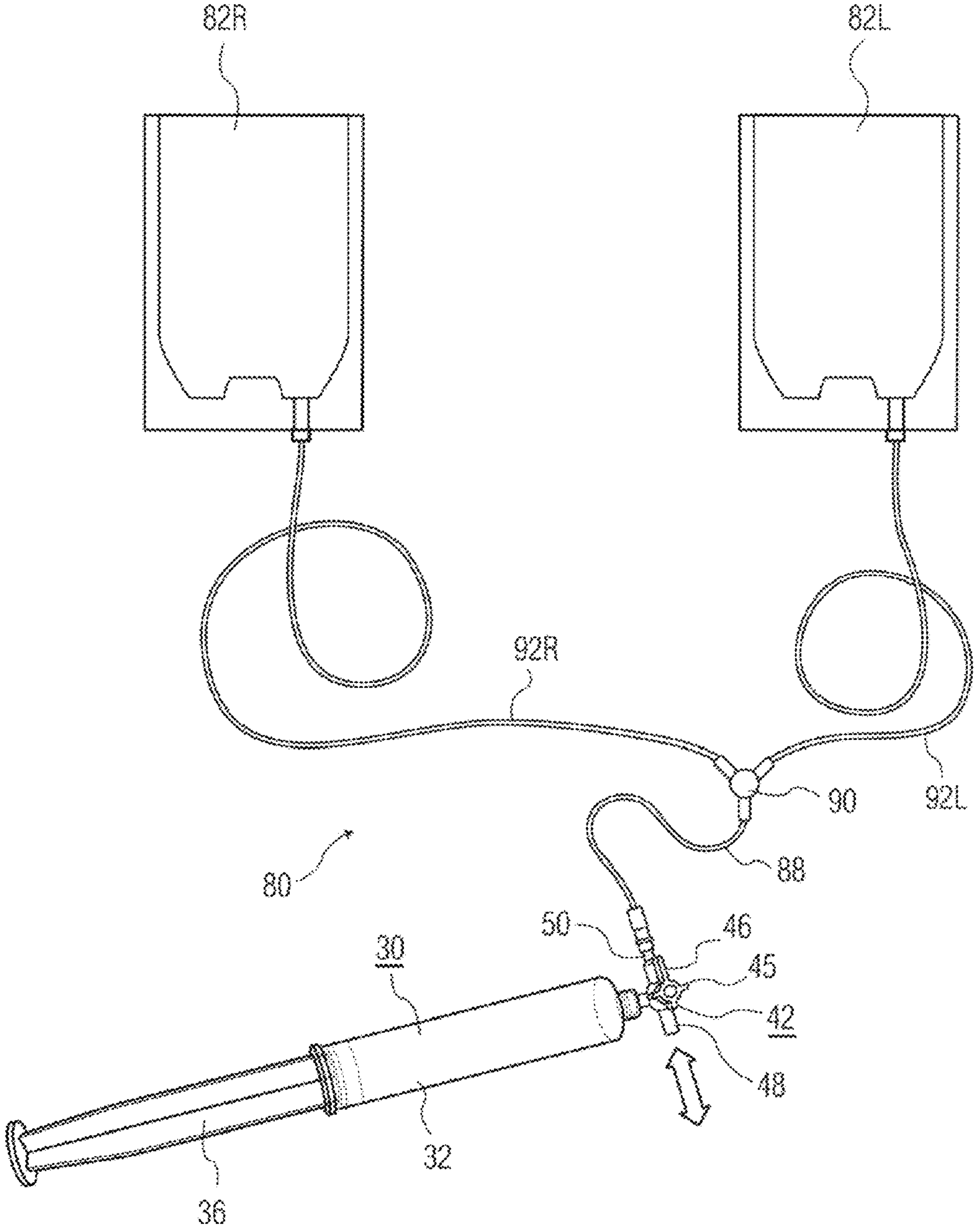
FIGS. 5 and 6 are isometric views of the device shown in FIG. 4 illustrating its component parts and the operation of the device.
Figure 6:
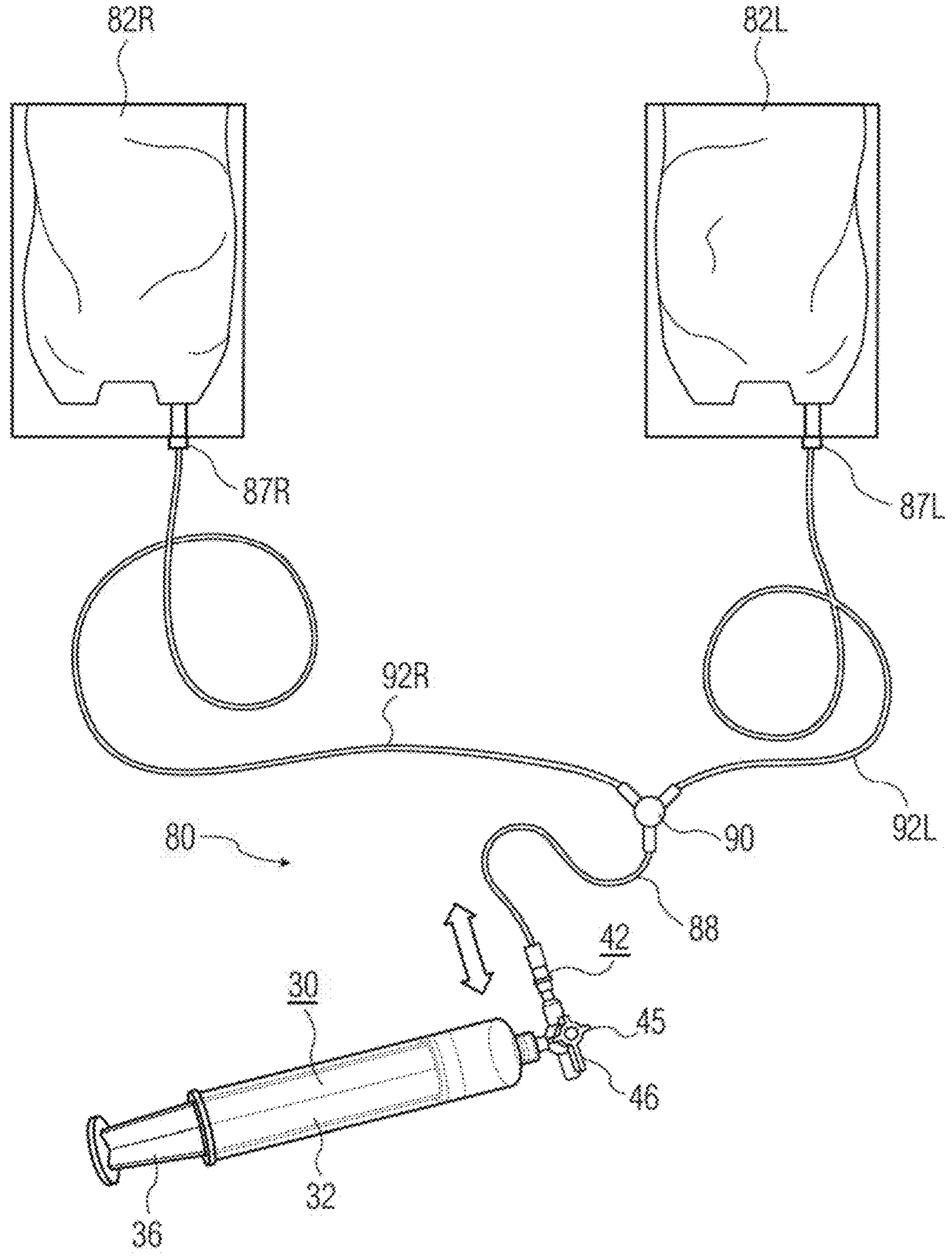

Referring to FIGS. 4-6, an embodiment according to a second aspect of the invention comprises a therapeutic jaw massaging device 80. In the embodiment depicted the device includes two flexible bladders 82*a* and 82*b* preferably made of a suitable plastic material. The material of the bladders can be chosen to ensure that it does not engender an allergic reaction in a user, since the bladders may come into contact with the user's skin even though they are placed in pockets in a head wrap as described further below.

The device 80 further includes a pneumatic pump in the form of a syringe 30 and valving arrangement 42 that can be identical to the syringe used in the embodiment described above in connection with FIGS. 1-3. In the massaging device, a tube 88 has one end connected to the valve passage 50 and its other end connected to a "Y" separator 90. Tubes 92R and 92L lead respectively from the separator 90 to the bladder fittings 87R and 87L, to which they are connected. In this fashion the interior of the syringe body 32 is connected in airtight relation to the interiors of the bladders 82R and 82L.

FIG. 4 shows the jaw massager 80 in use. A user P has a wrap W in place around his or her head. The wrap can be any material, but is preferably of a soft material such as a cotton-based textile that is comfortable against the user's skin, is generally non-allergenic, and can be readily laundered. Most conveniently, it will be generally flat and slightly elasticized, with closures at its ends for securing the ends together once the user has the wrap in place. The closures can take any form suitable to the purpose, but they will preferably be strips of Velcro® hook-and-eye material. The wrap W has pockets (omitted from the figures for ease of depiction) either interiorly or exteriorly of the wrap to hold the bladders 82R and 82L (the latter of which is not shown in FIG. 4) in place as shown against the user's jaw. Each pocket can be formed from a generally rectangular flat cloth with three sides sewn onto the wrap W so that the fourth open side accepts a bladder, or it can be a flat cloth with Velcro® material that adheres to Velcro® material on the wrap to permit different placements of the bladders to suit a user's needs.

The bladders 82R and 82L are prepared for use by emptying them of air. This can be done either by removing the syringe plunger from the syringe body or placing the valve in the intermediate position (see above) so that the interiors of the bladders are in communication with ambient air. The user then presses down with his or her hands on the bladders until the air in them is evacuated. The bladders are placed in the pockets in the wrap W and the wrap W is secured around the user with the bladders in the proper positions as shown in FIG. 4. Manipulation of the wrap and enabling it to be tightly secured in place on the user can be facilitated by making the wrap W of an elasticized material. The valve handle 46 is then rotated to its first position (FIG. 5) in which the interior of the syringe body is in communication with ambient air, as discussed above. The plunger is drawn outwardly, filling the syringe body with air. This state of the device is depicted in FIG. 5. The valve handle 46 is then rotated to its second position, seen in FIGS. 4 and 6, in which the syringe body is in airtight communication with the interior of the bladders through the tubes 88, 92*a* and 92*b*. The user can then inflate the bladders by moving the plunger inwardly (FIG. 6) and deflate them by moving the plunger outwardly. This alternately compresses and releases the muscles against which the bladders are held by the wrap to apply a massaging action.

The device 80 can include heat or cold packs that are held against the user's face by the wrap W while a massaging action is applied by the bladders. Hot or cold packs (not shown in the drawings) can be prepared in advance to permit both massaging of the jaw muscles simultaneously with the application of hot or cold therapy. The hot/cold packs would be of a conventional material that can be placed in a freezer or in a microwave oven to provide the appropriate thermal stimulation prior to using the jaw muscle massaging device. In a preferred embodiment the hot/cold packs would be specially designed to fit in the previously described pockets to be held between the air bladder in the pocket and the user's skin. Thus, when the user operates the device to perform jaw muscle massage as previously described, the hot/cold packs provide simultaneous application of heat or cold therapy to the muscles for added therapeutic benefit.

Accordingly, the jaw muscle massaging device as herein described is designed to provide the user with a simple method of massaging tight, sore, tender jaw muscles that are in a high state of tension, with the physical compression and subsequent relaxation of the jaw muscles though the inflation and deflation of the air bladders being under the sole control of the user. The insertion of hot and/or cold packs permits the user to simultaneously apply heat and massage or cold and massage to further apply these modalities to the jaw muscles.

While the above describes a particular embodiment of a jaw massaging device and a method for using same according to the present invention, it will be appreciated by those skilled in the art that the purposes and effects of the invention can be realized by embodiments other than the one described above. For example, the device just described could be used to massage jaw muscles (with or without hot/cold therapy) on only one side of the jaw. A device for such an application could have a suitable valve replacing the "Y" separator 90, so that an individual having spasm and/or tightness on only one side of the jaw could change the valve position so as to allow air to be directed only to one bladder, providing massage and hot/cold therapy just to muscles on the side of the jaw with the operative bladder. Alternatively, the user could apply the massage, with or without hot/cold therapy, to one side for a specified amount of time, and the change the valve handle 46 to apply the appropriate therapy to the other side of the jaw for a specified amount of time.

Jaw Exerciser/Massager

Another aspect of the invention involves using the jaw exerciser depicted in FIGS. 1-3 with the jaw massager depicted in FIGS. 4-6. One embodiment of such a combined device 100 is shown in use in FIG. 7.

The combined device 100 incorporates a jaw exerciser 10 and a jaw massager 80 in accordance with to the embodiments discussed above. They are identified in FIG. 7 with primes (') to denote that they differ from the above described structure in that the pneumatic pump arrangement is somewhat different from the arrangements discussed above in connection with each device configured for use on its own. However, identical parts are identified by the same reference numerals used above to avoid confusion.

Figure 7:
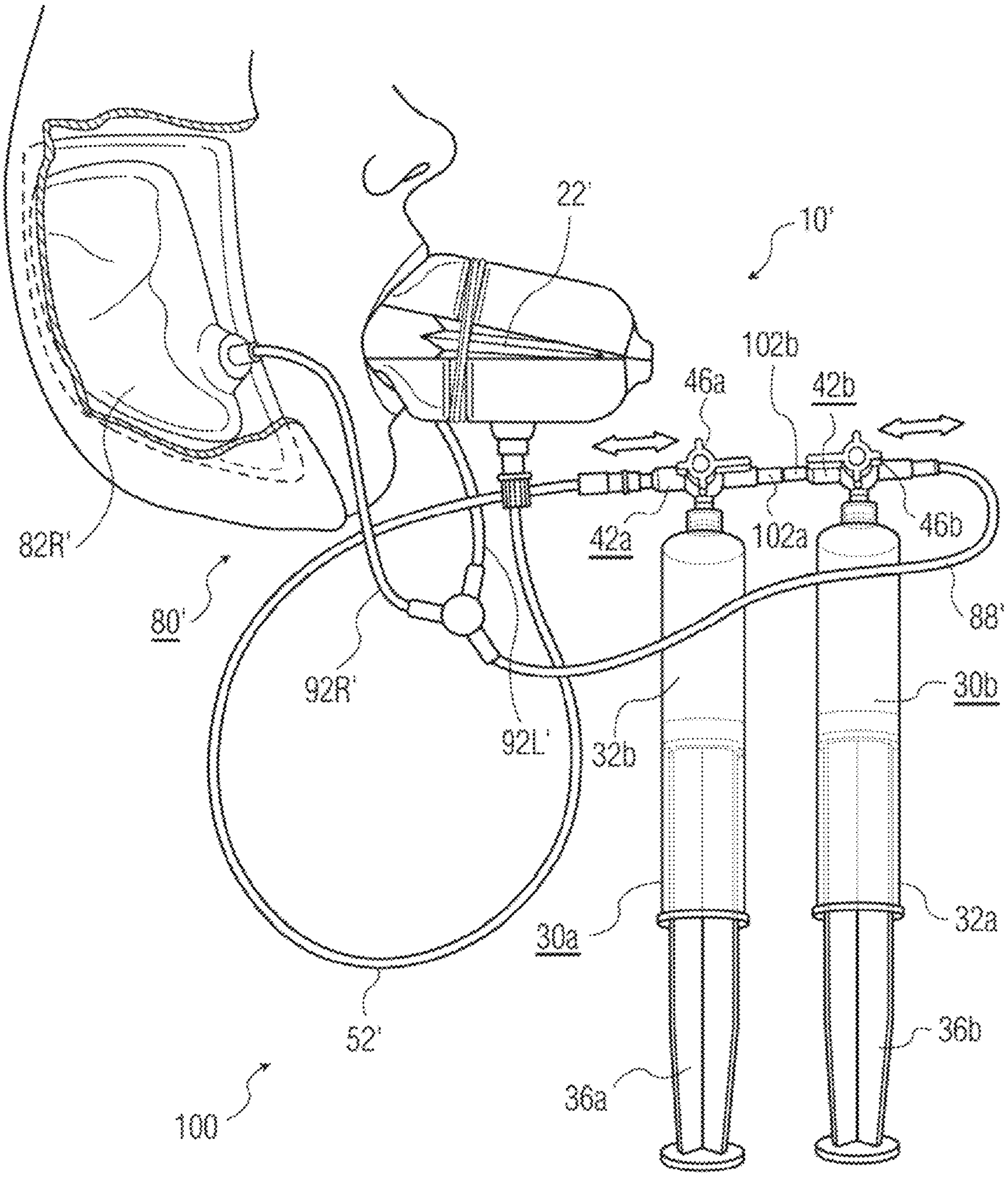
FIG. 7 is an isometric view of an embodiment of a therapeutic device that combines features of the device in FIGS. 1-3 and the device in FIGS. 4-6.

As shown in FIG. 7, the combined device comprises the jaw exercise device 10 with a syringe pump 30*a*, as described in detail above in connection with FIGS. 1-3, and the jaw massage device 80 with a syringe pump 30*b*, as described in detail above in connection with FIGS. 4-6. Each syringe pump 30*a* and 30*b* has a respective valve 42*a* and 42*b*. The valve passage 48 of each valve body that in the previously described embodiments was connected to ambient air are in the embodiment in FIG. 7 connected to each other through respective connector passages 102*a* and 102*b*. Placing the valve handles 46*a* and 46*b* in the positions shown in FIG. 7 thus permits simultaneous operation of both devices. For example, if the device 10' is set up in its jaw exercising configuration, depressing both syringe plungers 36*a* and 36*b* simultaneously (i) forces air into the bellows 22' and passively opens the jaw as described above, and (ii) forces air into the bladders 82' to massage the jaw muscles as described above (with or without optional not/cold therapy). Once the jaw is in the open position, the user can exercise the jaw muscles by closing against a resistance, which is controlled by the user using the syringe plunger 36*a* as discussed above, while the bladders are deflated by withdrawal of the plunger 36*b* by the user. It will be apparent from the present description that the apparatus can also be used in a manner in which the user closes his or her jaws by operating the syringe pump 30*b* to withdraw air from the bellows 22'.

Therefore, the combined use of the jaw exerciser and jaw muscle massager with application of hot/cold therapy provides the user with a combination of modalities that can be used simultaneously depending on the goal of the therapy. The numerous variations that exist with the combined device include:

1. Passive motion of the jaw joints (temporomandibular joints);
2. Active motion of the temporomandibular joints;
3. Active strengthening of jaw muscles;
4. Massage of jaw muscles, either unilaterally or bilaterally;
5. Hot compress therapy to the jaw muscles, either unilaterally or bilaterally;

6. Cold compress therapy to the jaw muscles, either unilaterally or bilaterally;
7. Sustained stretching of the jaw muscles, for a period of time determined by the user; and
8. Sustained maintenance of the temporomandibular joint in the maximum opening position for a sustained period of time determined by the user.

Of course, the above only describes one embodiment of a combined jaw exerciser/massager according to the present invention. It will be appreciated by those skilled in the art that the purposes and effects of the invention can be realized by embodiments other than the one described above. For example, if the user wants to simultaneously increase jaw range of motion and reduce jaw muscle spasm, the combined device can achieve this. The user would passively stretch the jaw open with the exerciser, and simultaneously provide massage and heat and/or ice to the jaw muscles. Alternatively, if the goal was to strengthen weak jaw muscles while reducing jaw muscle soreness, the user can actively close against the open exerciser (with control of the amount of resistance through the use of a predetermined number of elastic bands, as discussed further above), and simultaneously provide jaw muscle massage, with the option of hot and/or cold modalities.

Therefore, any combination of these modalities can be achieved with the device shown in FIG. 7 that combines a jaw exerciser and jaw muscle massager with the option of hot/cold application depending on the goals and needs of the user.

Mandible Translation Adapter

Figure 8:
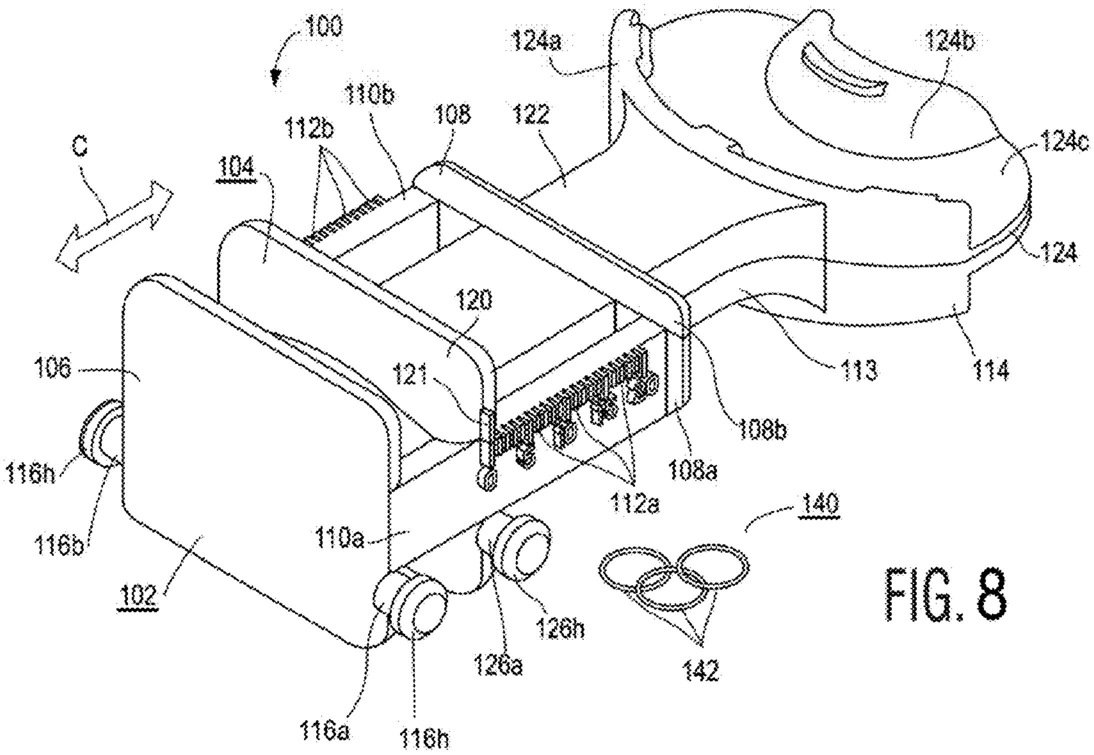
FIG. 8 is an isometric view of a mandible translation adapter according to one embodiment of the invention.

FIG. 8 is an isometric view of a mandible translation adapter 100 according to an embodiment of the invention that is especially adapted to be used with the therapeutic exercising device 10 depicted in FIGS. 1-3. It is preferably made of a moldable biocompatible plastic resin that is non-ferrous and transparent to imaging systems such as magnetic resonance imaging, which will render it suitable for implementation of an optional application of the translation adapter described further below. One suitable material is polyoxymethylene in the form sold as Delrin® acetyl resin by E. I. du Pont de Nemours and Company of Wilmington, Del. The translation adapter 100 comprises a mandible frame 102 and a maxilla frame 104 that mount together for relative sliding movement to and fro in the direction of arrow C. The mandible frame 102 has a rear actuating plate 106 and a front guide 108 rigidly connected together at their respective lateral sides by a connecting frame comprising first and second frame parts 110*a* and 110*b*. The outer surfaces of the connecting frame parts 110*a* and 110*b* are optionally molded with raised, regularly spaced measuring indicia 112*a* and 112*b*, which are numbered at predetermined intervals. In the embodiment shown in FIG. 8 the leftmost indicia (as seen on connecting frame part 110*a*) is labeled "0," and every fifth indicia proceeding rightward is labeled as shown with a "5", 10," etc. The numbers labeling the indicia are preferably molded into the surfaces of the connecting frame parts at the time of manufacture. Most conveniently, the indicia are provided at 1 mm intervals.

Figure 9:
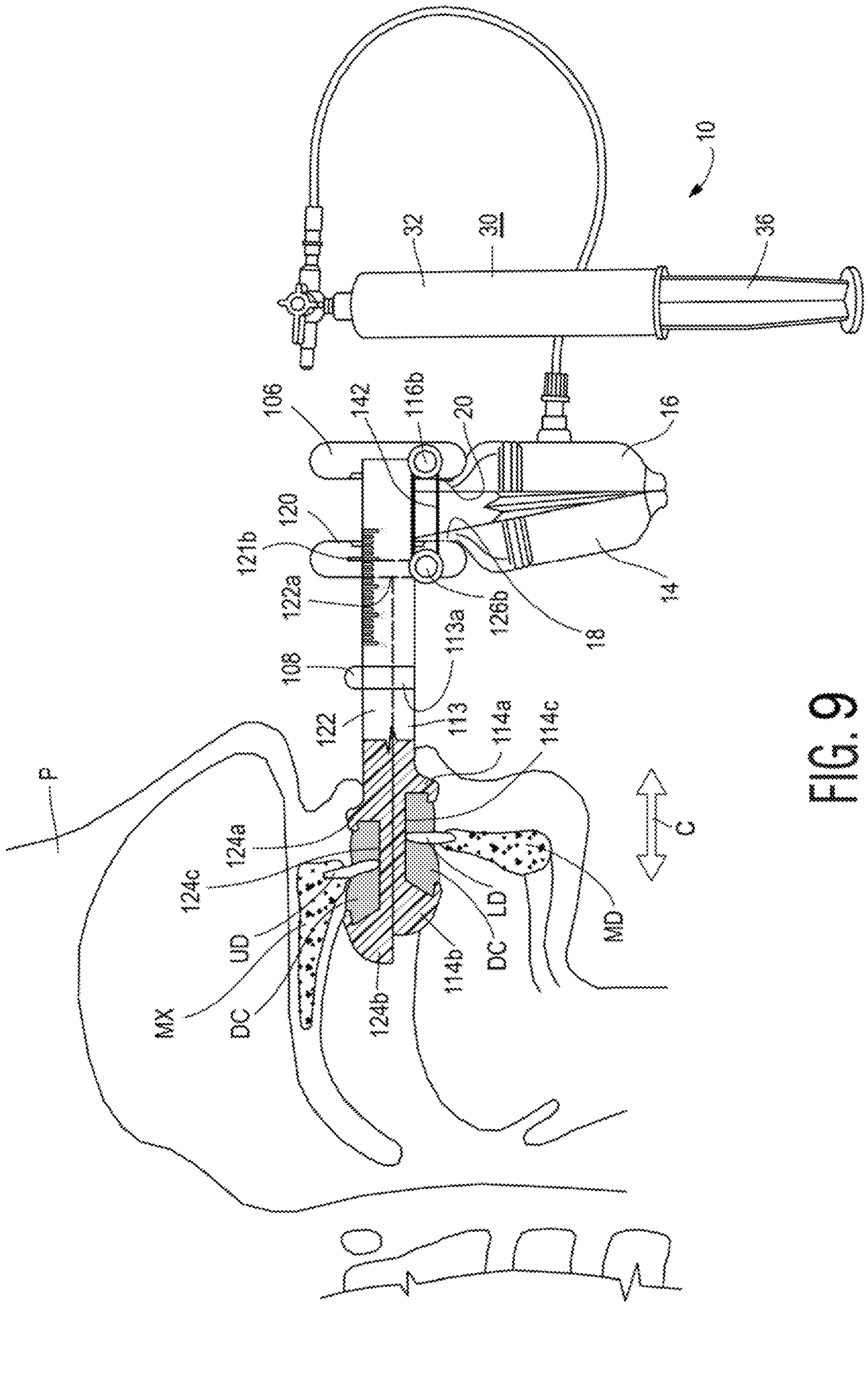
FIG. 9 is a modified cross sectional view of a person's head with the translation adapter shown in FIG. 8 mounted on the device shown in FIG. 1 and in place holding a user's mandible in a forward translated position.

A number of other parts of the mandible frame 102 are important to the mandible translation adapter aspect of the present invention. A mandible actuating arm 113 extends from a proximal end 113*a* (see FIG. 9), where it is molded as part of the front guide 108, to a distal end that carries a mandible retaining plate 114. The mandible retaining plate 114 includes a buccal mandible retainer 114*a*, a lingual mandible retainer 114*b*, and a flat arcuate portion 114*c* for accepting at least part of the user's mandibular dentition. FIG. 9 shows the relation of these parts of the mandibular retaining plate 114 to the user's mandibular dentition LD when the translation adapter 100 is in use. The rear actuating plate 106 includes integrally molded posts 116*a* and 116*b* extending outwardly transverse to the direction of relative movement of the mandible frame 102 and the maxilla frame 104 (arrow C). The function of these parts in the use of the translation adapter 100 is described below.

The maxilla frame 104 is typically molded as integral part, using the same material as the mandible frame 102 for ease and convenience of manufacture. It comprises a maxilla frame bearing plate 120 and a maxilla contacting arm 122. The maxilla frame bearing plate 120 optionally includes indexing rib 121*a* and 121*b* on either side (see FIG. 9). When the frame parts 102 and 104 are assembled, a corresponding rib 121*a* or 121*b* is adjacent to measuring indicia 112*a* or 112*b* extending along the connecting frame parts 110*a* and 110*b* of the mandible frame 102. The position of the indexing ribs 121*a* and 121*b* thus indicates the amount of relative movement of the mandible frame 102 and the maxilla frame 104. The measuring indicia 112 and the indexing ribs 121 are raised from the surrounding surfaces of the parts carrying them so that they are more easily read, but it will be appreciated that they could take other forms, such as imprinted markings. The mandible frame preferably includes a suitable stop (not shown) that engages the maxilla frame bearing plate 120 to establish a "closed" position in which the indexing ribs 121 are adjacent the respective "0" indicia 112, with the mandible retaining plate 114 and maxilla retaining plate 124 aligned as seen in FIG. 8. If desired, a suitable detent arrangement can be provided to provide the user with a tactile/audible indication that the translation adapter is in the "closed" position and to hold the adapter frames 102 and 104 in that orientation against inadvertent relative movement.

The maxilla contacting arm 122, which is an important component of the mandible translation adapter aspect of the present invention, extends from a proximal end 122*a* (see FIG. 9) to a distal end that carries a maxilla retaining plate 124. The maxilla retaining plate 124 includes a buccal maxilla retainer 124*a*, a lingual maxilla retainer 124*b*, and a flat arcuate portion 124*c* for accepting at least part of the user's maxillary dentition UD. FIG. 9 shows the relation of these parts of the maxilla retaining plate 124 to the user's maxillary dentition when the translation adapter 100 is in use. It will be further understood that the configuration of the mandible retaining plate 114 corresponds to that of the maxilla retaining plate 124, so that one skilled in the art will be able to construct a mandible retaining plate 114 without further illustration or description of its buccal and lingual retainers or the dentition-accepting flat portion therebetween, particularly in view of the detailed description that follows of the manner in which the translation adaptor is used. In addition to the maxilla contacting arm, the maxilla frame bearing plate 120 includes integrally molded posts 126*a* and 126*b* (see FIG. 9) extending outwardly from both sides of the bearing plate transverse to the direction of relative movement of the mandible frame 102 and the maxilla frame 104 (arrow C).

The posts 116 and 126 form part of a user-adjustable biasing arrangement 140 that in the present embodiment further includes a plurality of elastic members 142. In similar fashion to the jaw exerciser 10 embodiment described already, the elastic members 142 resemble rubber bands, although they may be made of different materials for reasons related to their use in the present invention. As discussed, it may be necessary to make the elastic members 142 of a material that accounts for any user allergies. In use the elastic members 142 fit over the posts 116 and 126 on either side of the translation adapter, as best seen in FIG. 9. The posts typically include enlarged heads 116*h* and 126*h* for retaining the elastic members 142 on the posts once they are put in place by the user. They are under tension when in place and each provides a predetermined amount of force biasing the mandible frame's rear actuating plate 106 and the maxilla frame bearing plate 120 together. The elastic members 142 will preferably have the same properties as the elastic members 62 discussed above and thus will most conveniently be made of the same silicone, latex-free elastic. From the description herein, including the description of the use of the translation adapter, those skilled in the art will appreciate that the biasing arraignment can have other configurations within the scope of the invention. For example, coiled tension springs of varying spring constants or different numbers of tension springs could be used to provide the biasing force that comprises this aspect of the invention.

The mandible frame 102 and the maxilla frame 104 can be assembled in any manner preferred by one skilled in the art, and it will be readily apparent that there are many ways of constructing a mandible translation adapter with the salient features just described and depicted in the drawings. For example, one manner of constructing the translation adapter would make the front guide 108 in a main guide section 108*a* and a separate guide closure 108*b*. In this example, the maxilla contacting arm 122 is placed in face-to-face contact with the mandible actuating arm 113. With the parts thus in place, the front guide closure 108*b* would be secured in place on the main guide section 108*b* in any suitable fashion, preferably by a suitable adhesive. Fasteners could also be used either instead of or in addition to an adhesive, although non-ferrous fasteners would be required for the optional use of the translation adapter discussed below in connection with FIG. 10.

FIG. 9, which is a cross section of the head of a user P showing the mouth parts in schematic cross section, illustrates the translation adapter 100 in use in combination with the jaw exercising device 10 described previously. Preferably, the mandible retaining plate 114 and the maxilla retaining plate 124 are prepared by filling the arcuate portions 114*c* and 124*c* between the respective buccal retainers 114*a* and 124*a* and lingual retainers 114*b* and 124*b* with a dental impression composition DC such as Blu-Mousse® vinyl polysiloxane impression material, available from Parkell, Inc., of Edgewood, N.Y. With the mandible frame 102 and maxilla frame 104 in their "closed" position against the stop discussed above so that the indexing rib 121 is at its "0" position as indicated by the indicia 112, an impression is taken of the user's upper and lower dentition, and the impression composition is subsequently cured. Thus, when the translation adapter is in place for use, with one or more elastic members 142 biasing the actuating plate 106 and the bearing plate 120 together against the stop described above, the adapter 100 will start from a "neutral" position in which the user's mandible is in the position it occupies in its natural state.

One of the principal advantages of the mandibular translation adapter 100 is that in a preferred embodiment it can be used with the jaw exercising device 10 for exercise and therapy of the jaw muscles and surrounding tissues involved in posterior-anterior movement of the mandible. This can be appreciated from FIG. 9, in which the maxilla MX of the user P is seen to include upper, maxillary dentition UD, and the mandible MD includes lower, mandibular dentition LD. The cured dental impression composition DC securely holds the dentition in place on the mandible retaining plate 114 and the maxilla retaining plate 124 so that the user's mandible and maxilla are properly positioned during an exercise. To perform an exercise using the translation adapter 100, the jaw exercising device 10 is coupled to the mandibular translation device 100 with the bite platforms 18 and 20 of the first and second bite members 14 and 16 disposed between the rear mandible actuating plate 106 and the maxilla bearing plate 120. In a preferred embodiment the facing surfaces of the actuating plate 106 and the bearing plate 120 are contoured to match the shape of the bite platforms 18 and 20 to provide a more secure interconnection between the exercising device 20 and the translation adapter 100. The actuating plate 106 and the bearing plate 120 are urged apart in the direction of arrow C by the built-in bias-open force exerted on the bite members 14 and 16, as discussed above, but at least one or more of the elastic members 142 is placed around the posts 116 and 126 for providing a counter-force that holds the actuating plate 106 and the bearing plate 120 together in their "closed" position.

The translation adapter 100 is capable of providing a variety of exercise modalities in this configuration. One basic modality involves passive stretching of the temporomandibular joint in the anterior-posterior direction. In this exercise, repeatedly pressing the syringe plunger 36 into the syringe body 30 moves the mandibular actuating plate 106 and the maxilla frame bearing plate 120 apart and thus causes the mandible to protrude in the anterior direction to a position such as that illustrated in FIG. 9. The one or more elastic bands 142 around the posts 116 and 126 urge the mandible actuating plate 106 and the maxilla frame bearing plate 120 back together to return to their starting position. The user can control the rate of return with the syringe plunger 36, by modulating the force exerted by the bite members 14 and 16 resisting this return motion. The exercise can be repeated as many times as desired and the user can control both the amount of anterior protrusion of each stroke of each repetition and the rate of return toward the starting position.

The elastic bands 142 also permit the translation adapter 100 to be used for actively exercising the temporomandibular joint in the anterior-posterior direction. That is, the user can place a number of elastic bands over the posts 116 and 126 in accordance with the resistance desired, Either with or without the assistance of the jaw exercising device 10, the user can move his or her mandible forward against the resistance provided by the one or more elastic bands. The user can hold the mandible in place against the resistance for a desired length of time and then permit it to return to the normal position. Having the jaw exercising device in place as shown in FIG. 9 permits the user to control the rate at which his or her mandible returns to the normal position, as well as acting as a safety device to hold the mandible in place in the event that the user feels any discomfort during the exercise. It will also be appreciated that the bite platforms 18 and 20 can be inserted from above (as seen in FIG. 9) into the space between the mandible actuating plate 106 and the maxilla frame bearing plate 120. This increases the versatility of the translation adapter since the user can use it in either orientation. For example, if the adapter is to be used in a diagnostic imaging application such as that discussed just below, having the bite platforms inserted superiorly between the actuating plate 106 and the maxilla bearing plate 120 enables the device to be used with imaging devices that would not permit the user to be properly positioned relative to the device if the bite members 14 and 16 are inserted inferiorly (the orientation depicted in FIG. 9). Preferably, the facing surfaces of the actuating plate 106 and the bearing plate 120 are contoured to match the shape of the bite platforms 18 and 20 when they are in the superior orientation as well as in the inferior orientation, as discussed above.

Figure 10A:
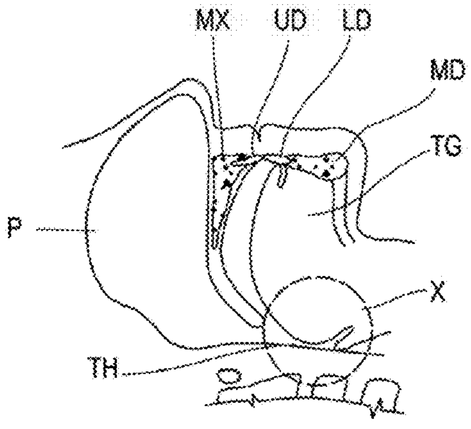
FIG. 10 comprises FIGS. 10A and 10B, which are schematic cross sectional views of the head of a person lying supine, FIG. 10A showing the mouth parts in a position in which the airway to the lungs is blocked, as when the person is sleeping on his or her back, and FIG. 10B showing the mandible translated forward to open the blocked airway.
Figure 10B:
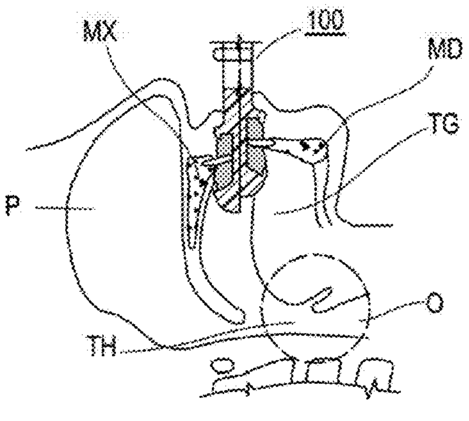

FIGS. 10A and 10B illustrate an optional application of the translation adapter 100 that utilizes the optional measuring indicia 112 and indexing rib 121 described above. This application enables a clinician to determine with precision the amount of anterior mandible translation should be imparted by a commercially available mandible repositioning appliance held by the user in his or her mouth while sleeping. FIG. 10A is a schematic cross section of the mouth and throat of a supine sleeping person P suffering from obstructive sleep apnea (OSA). The sleeper's tongue TG relaxes against the back of his or her throat TH and obstructs the airway to the lungs, as indicated by the circled region labeled "X." This causes the person to wake momentarily because the air supply to his or her lungs has been cut off, which is a characteristic of OSA. This movement of the tongue, and posterior mouth parts such as the uvula (not shown in the drawings), also causes snoring, which can also wake the sleeper and/or those near him or her.

In contrast, FIG. 10B shows the person with the translation adapter 100 in place. In this application the adapter 100 is in use in a clinical setting in which the user is in a diagnostic imaging device such as a magnetic resonance imaging apparatus (not shown), and with his or her mandible translated forward using the adapter. By constructing the translation adapter 100 entirely of non-ferrous materials, it can be used to determine the minimum amount the mandible MD must be translated anteriorly to maintain the person's throat open, as shown by the letter "O." When the appropriate translation amount is determined from the MRI images, the measuring indicia 112 at which the indexing rib 121 is located can be used to construct a mandible translation appliance such as the SomnoDent® mandibular advancement device, sold by SomnoMed Ltd., Crow's Nest, Australia, believed also to be disclosed in U.S. Pat. No. 6,604,527, assigned to SomnoMed Ltd. Another example of a known dental appliance for treating OSA is shown in U.S. Pat. No. 5,365,945. These patents are incorporated in this description by reference as if disclosed in full herein. An appliance such as these can then be constructed to provide the amount of anterior displacement to be imparted to the user's mandible as determined from the MRI images taken using the translation adapter 100 in accordance with an embodiment of the present invention. Conveniently, the jaw exercising device 10 can be used to incrementally translate the user's mandible forward during the imaging process. If that is the case, its parts will be also be made from a suitable non-ferrous material, which can be the same material used to make the translation adapter 100.

A translation adapter in accordance with the present invention provides foremost a device for exercising a user's jaw muscles by movement of the user's mandible against resistance in the anterior direction, while at the same time permitting the passive stretching of the jaw muscles in the same direction offered by prior art mandible translation devices. In addition, the translation adapter is made even more versatile by including measuring indicia for fitting an mandibular repositioning appliance that provides the minimum amount of anterior translation to achieve its purpose and thus avoids unnecessary stress on the user's jaw.

Summary

The present invention provides a user with a wide variety of therapeutic options. As discussed in the above Background section, prior devices, while generally effective for the purposes for which they were intended, do not provide the flexibility of operation that is most advantageous in developing a program of therapy for the wide variety of existing jaw and facial conditions. The various devices and their variations as described herein, and the methods of using them, provide a medical practitioner with myriad therapeutic options, and provide the capability of changing therapies for any particular individual as his or her recovery or therapy progresses.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A mandibular translation apparatus for translating a user's mandible in an anterior direction, the apparatus comprising;

a mandible frame including a mandible actuating plate and a mandible actuating arm having a mandible retainer at the distal end thereof adapted for engaging the user's mandible;

a maxilla frame including a maxilla bearing plate and a maxilla contacting arm having at a distal end thereof a maxilla retainer for engaging the user's maxilla, wherein the mandible frame and the maxilla frame are connected for relative movement of the mandible retainer and the maxilla retainer in a first direction toward a position wherein the user's mandible is protruded anteriorly relative to the user's maxilla;

an adjustable biasing arrangement for exerting a force determined by the user on the mandible frame and maxilla frame in a second direction opposite to the first direction; and an actuating device for moving the mandible frame and maxilla frame relative to each other in the first direction, the actuating device comprising:

two actuating members, each having a portion for insertion between the mandible actuating plate and the maxilla bearing plate, an expandable enclosure that expands and contracts between the actuating members when air is introduced into and released from the interior of the enclosure, wherein expanding the enclosure exerts an opening force on the actuating members for moving the mandible retainer and the maxilla retainer in the first direction, and a user-operated pneumatic pump connected to the expandable enclosure for introducing air under pressure into the expandable enclosure to move the mandible retainer and the maxilla retainer in the first direction against the force exerted thereon in the second direction.

2. An apparatus as in claim 1, wherein the adjustable biasing arrangement includes a plurality of elastic bands constructed for individual placement by the user between the mandible frame and the maxilla frame and the force in the second direction is determined by the number of elastic members attached to the frames.

3. An apparatus as in claim 2, wherein the pneumatic pump comprises a syringe with a hollow syringe body in communication with the expandable enclosure and a syringe plunger movable by the user in the syringe body to force air into and extract air from the expandable enclosure.

4. An apparatus as in claim 1, the actuating device of which being usable separately as a therapeutic exercising device for increasing temporomandibular joint range of motion of a user, wherein:

the actuating members comprise bite members, each having a bite portion adapted for insertion into the user's mouth to engage upper and lower teeth of the user, respectively; and introducing air into the interior of the enclosure exerts an opening force for moving the bite members relative to each other toward an open position in which the bite portions separate the upper and lower jaws of the user.

5. An apparatus as in claim 4, wherein facing surfaces of the mandible actuating plate and the maxilla frame conform to the contour of the portion of the bite members in contact therewith.

6. An apparatus as in claim 4, the actuating device of which being usable separately as a therapeutic exercising device for simultaneously increasing temporomandibular joint range of motion and strengthening jaw muscles of a user, wherein the actuating device further comprises:

a spring exerting a predetermined force biasing the bite members toward the open position; and a second adjustable biasing arrangement for exerting a closing force determined by the user on the bite members against the predetermined force biasing the bite members toward the open position, wherein the pneumatic pump is operable to move the members toward the open position when the closing force magnitude is sufficient to overcome the opening force biasing the bite members toward the open position.

7. An apparatus as in claim 6, wherein the second adjustable biasing arrangement includes a plurality of elastic bands constructed for individual placement by the user around the bite members and the closing force is determined by the number of elastic members attached to the bite members.

8. An apparatus as in claim 6, wherein the expandable enclosure includes a bellows that comprises the spring for exerting the predetermined force biasing the bite members toward the open position.

9. An apparatus as in claim 6, wherein the spring exerts the predetermined force directly on the bite members.

10. An apparatus as in claim 9, wherein the bite members are connected by a hinge and the spring is a torsion spring associated with the hinge.

11. An apparatus as in claim 9, wherein the spring is a compression spring disposed between the bite members.

12. An apparatus as in claim 6 for simultaneously increasing temporomandibular joint range of motion and massaging and strengthening jaw muscles of the user, the apparatus further comprising:

at least two hollow bladders that expand when air under pressure is introduced into the interior of the bladders and contract when the air under pressure is released from the interior of the bladders; and a wrap adapted for holding the bladders in place against opposite sides of the user's face proximate to jaw muscles of the user, wherein the pneumatic pump is connected to the bladders for introducing air under pressure into the interiors thereof to expand the bladders and compress jaw muscles of the user when the bladders are held in place by the wrap and for withdrawing air from the bladders for contraction thereof.

13. An apparatus as in claim 12, wherein the expandable enclosure includes a bellows.

14. An apparatus as in claim 12, wherein the pneumatic pump comprises a first syringe with a hollow syringe body in communication with the expandable enclosure and a syringe plunger movable by the user in the syringe body to force air into and extract air from the expandable enclosure and a second syringe with a hollow syringe body in communication with the hollow bladders and a syringe plunger movable by the user in the syringe body to force air into and extract air from the hollow bladders.

* * * * *